(12) United States Patent
Sablone et al.

(10) Patent No.: US 8,672,824 B2
(45) Date of Patent: Mar. 18, 2014

(54) PROCESS AND EQUIPMENT FOR FOLDING A PANT TYPE DIAPER

(75) Inventors: Gabriele Sablone, Montesilvano (IT); Paolo Pasqualoni, San Giovanni Teatino (IT)

(73) Assignee: Fameccanica.Data S.p.A., Sambuceto di San Ginvanni Teatino (Chieti) (IT)

(*) Notice: Subject to any disclaimer, the term of this patent is extended or adjusted under 35 U.S.C. 154(b) by 209 days.

(21) Appl. No.: 13/422,248

(22) Filed: Mar. 16, 2012

(65) Prior Publication Data

US 2012/0238431 A1  Sep. 20, 2012

Related U.S. Application Data

(60) Provisional application No. 61/453,677, filed on Mar. 17, 2011.

(51) Int. Cl.
*B31B 1/26* (2006.01)

(52) U.S. Cl.
USPC ............................................. 493/441; 493/423

(58) Field of Classification Search
CPC .............. B31B 1/02; B31B 1/25; B31B 1/26; B31B 1/28; B31B 1/36; B31B 1/58; B31B 2201/2683; B31B 2201/2637; B31B 2201/25; A61F 13/15764; A61F 13/15747; A61F 13/565; A61F 13/62
USPC .......... 493/423, 424, 441, 401, 374; 156/227, 156/229, 161, 163, 164; 428/89–100, 428/195.1, 198
See application file for complete search history.

(56) References Cited

U.S. PATENT DOCUMENTS

| | | | |
|---|---|---|---|
| 4,022,456 A | 5/1977 | Hooper et al. | |
| 4,081,301 A | 3/1978 | Buell | |
| 4,610,680 A | 9/1986 | LaFleur | |
| 4,650,173 A | 3/1987 | Johnson et al. | |
| 4,699,622 A | 10/1987 | Toussant et al. | |

(Continued)

FOREIGN PATENT DOCUMENTS

| | | |
|---|---|---|
| EP | 0983760 | 3/2000 |
| EP | 1772403 A1 | 4/2007 |

(Continued)

OTHER PUBLICATIONS

International Search Report and Written Opinion for PCT/IB2012/000520 mailed Jun. 6, 2012.

(Continued)

*Primary Examiner* — Hemant M Desai

(74) *Attorney, Agent, or Firm* — Sutherland Asbill & Brennan LLP

(57) ABSTRACT

A method and apparatus for folding and engaging side panels of a training pant are provided. The training pant comprises a leading portion, a trailing portion, a central portion, and a first pair of side panels and a second pair of side panels attached to the central portion. The central portion of the training pant is folded about a transverse axis to form a folded training pant. Portions of the first pair of side panels and second pair of side panels are engaged while the central portion of the folded training pant is received by at least one recessed seat. The at least one recessed seat is located on at least one of a first belt and a second belt of a conveyance system.

67 Claims, 4 Drawing Sheets

(56) References Cited

U.S. PATENT DOCUMENTS

| | | | |
|---|---|---|---|
| 4,701,156 A * | 10/1987 | Larsonneur | 493/418 |
| 4,717,375 A * | 1/1988 | Lundmark | 493/360 |
| 4,738,440 A | 4/1988 | Weir | |
| 4,761,937 A | 8/1988 | Francioni | |
| 4,834,736 A | 5/1989 | Boland et al. | |
| 4,834,738 A | 5/1989 | Kielpikowski et al. | |
| 4,908,247 A | 3/1990 | Baird et al. | |
| 4,938,753 A | 7/1990 | Van Gompel et al. | |
| 4,940,464 A | 7/1990 | Van Gompel et al. | |
| 5,046,272 A | 9/1991 | Vogt et al. | |
| 5,087,253 A | 2/1992 | Cooper | |
| 5,092,862 A | 3/1992 | Muckenfuhs et al. | |
| 5,147,343 A | 9/1992 | Kellenberger | |
| 5,156,902 A | 10/1992 | Pieper et al. | |
| 5,176,615 A * | 1/1993 | Munsch | 493/427 |
| 5,213,645 A | 5/1993 | Nomura et al. | |
| 5,259,902 A | 11/1993 | Muckenfuhs | |
| 5,269,776 A | 12/1993 | Lancaster et al. | |
| 5,286,543 A | 2/1994 | Ungpiyakul et al. | |
| 5,383,872 A | 1/1995 | Roessler et al. | |
| 5,435,802 A | 7/1995 | Kober | |
| 5,476,053 A | 12/1995 | Brocklehurst | |
| 5,496,298 A | 3/1996 | Kuepper et al. | |
| 5,542,942 A | 8/1996 | Kline et al. | |
| 5,556,360 A | 9/1996 | Kober et al. | |
| 5,556,504 A | 9/1996 | Rajala et al. | |
| 5,569,234 A | 10/1996 | Buell et al. | |
| 5,601,542 A | 2/1997 | Melius et al. | |
| 5,626,711 A | 5/1997 | Herrmann | |
| 5,649,920 A | 7/1997 | Lavon et al. | |
| 5,669,996 A | 9/1997 | Jessup | |
| 5,702,551 A | 12/1997 | Huber et al. | |
| 5,745,922 A | 5/1998 | Rajala et al. | |
| 5,765,495 A | 6/1998 | Adamski, Jr. | |
| 5,772,825 A | 6/1998 | Schmitz | |
| 5,776,389 A | 7/1998 | Chaudhary | |
| 5,779,831 A | 7/1998 | Schmitz | |
| 5,788,805 A | 8/1998 | Herrmann | |
| 5,795,433 A | 8/1998 | Niedermeyer | |
| 5,797,831 A | 8/1998 | Roberts et al. | |
| 5,803,448 A | 9/1998 | Stiel et al. | |
| 5,836,932 A | 11/1998 | Buell et al. | |
| 5,865,135 A | 2/1999 | Price et al. | |
| 5,904,802 A | 5/1999 | Niedermeyer | |
| 5,915,319 A | 6/1999 | Price et al. | |
| 5,916,203 A | 6/1999 | Brandon et al. | |
| 5,919,334 A | 7/1999 | Niedermeyer | |
| 5,938,652 A | 8/1999 | Sauer | |
| 5,940,887 A | 8/1999 | Rajala et al. | |
| 5,980,439 A | 11/1999 | Johnson et al. | |
| 6,015,934 A * | 1/2000 | Lee et al. | 604/358 |
| 6,022,431 A | 2/2000 | Blenke et al. | |
| 6,022,432 A | 2/2000 | Elsberg et al. | |
| 6,027,440 A | 2/2000 | Roth | |
| 6,036,805 A | 3/2000 | McNichols | |
| 6,098,203 A | 8/2000 | Rajala et al. | |
| 6,113,717 A | 9/2000 | Vogt et al. | |
| 6,210,388 B1 | 4/2001 | Widlund et al. | |
| 6,213,991 B1 | 4/2001 | Kling et al. | |
| 6,248,098 B1 | 6/2001 | Sayama | |
| 6,260,211 B1 | 7/2001 | Rajala et al. | |
| 6,264,639 B1 | 7/2001 | Sauer | |
| 6,264,643 B1 | 7/2001 | Toyoda | |
| 6,307,119 B1 | 10/2001 | Cammarota et al. | |
| 6,328,725 B2 | 12/2001 | Fernfors | |
| 6,395,115 B1 | 5/2002 | Popp et al. | |
| 6,402,731 B1 | 6/2002 | Suprise et al. | |
| 6,432,243 B1 | 8/2002 | Popp et al. | |
| 6,432,248 B1 | 8/2002 | Popp et al. | |
| 6,447,497 B1 | 9/2002 | Olson | |
| 6,447,628 B1 | 9/2002 | Couillard et al. | |
| 6,454,751 B1 | 9/2002 | Olson | |
| 6,454,752 B1 | 9/2002 | Huang et al. | |
| 6,461,343 B1 | 10/2002 | Schaefer et al. | |
| 6,461,344 B1 | 10/2002 | Widlund et al. | |
| 6,461,471 B1 | 10/2002 | Tharpe, Jr. et al. | |
| 6,475,205 B2 | 11/2002 | Shimada et al. | |
| 6,497,032 B2 | 12/2002 | Maxton et al. | |
| 6,500,161 B1 | 12/2002 | Freiburger et al. | |
| 6,513,221 B2 | 2/2003 | Vogt et al. | |
| 6,514,187 B2 | 2/2003 | Coenen et al. | |
| 6,524,293 B1 | 2/2003 | Elsberg et al. | |
| 6,531,015 B1 | 3/2003 | Gardner, Jr. | |
| 6,562,167 B2 | 5/2003 | Coenen et al. | |
| 6,565,691 B2 | 5/2003 | Tomsovic et al. | |
| 6,575,953 B2 | 6/2003 | Olson | |
| 6,579,275 B1 | 6/2003 | Pozniak et al. | |
| 6,596,107 B2 | 7/2003 | Stopher | |
| 6,596,113 B2 | 7/2003 | Csida et al. | |
| 6,613,033 B1 | 9/2003 | Popp et al. | |
| 6,635,135 B2 | 10/2003 | Kuen et al. | |
| 6,645,190 B1 | 11/2003 | Olson et al. | |
| 6,648,871 B2 | 11/2003 | Kusibojoska et al. | |
| 6,652,696 B2 | 11/2003 | Kuen et al. | |
| 6,667,085 B1 | 12/2003 | McNichols | |
| 6,669,618 B2 | 12/2003 | Reising et al. | |
| 6,682,626 B2 | 1/2004 | Minar et al. | |
| 6,702,798 B2 | 3/2004 | Christoffler et al. | |
| 6,708,855 B2 | 3/2004 | Wilson et al. | |
| 6,723,034 B2 | 4/2004 | Durrance et al. | |
| 6,723,035 B2 | 4/2004 | Franklin et al. | |
| 6,730,188 B2 | 5/2004 | Sanders | |
| 6,743,321 B2 | 6/2004 | Guralski et al. | |
| 6,752,796 B2 | 6/2004 | Karami | |
| 6,761,711 B1 | 7/2004 | Fletcher et al. | |
| 6,764,475 B1 | 7/2004 | Olson | |
| 6,776,316 B2 | 8/2004 | Van Eperen et al. | |
| 6,793,650 B2 | 9/2004 | Weber | |
| 6,808,787 B2 | 10/2004 | Coenen et al. | |
| 6,817,994 B2 | 11/2004 | Popp et al. | |
| 6,821,370 B2 | 11/2004 | Tomsovic et al. | |
| 6,846,374 B2 | 1/2005 | Popp et al. | |
| 6,849,067 B2 | 2/2005 | Fletcher et al. | |
| 6,854,624 B2 | 2/2005 | Vogt et al. | |
| 6,872,267 B2 | 3/2005 | Popp et al. | |
| 6,878,223 B2 | 4/2005 | Kuen et al. | |
| 6,885,451 B2 | 4/2005 | Vogt et al. | |
| 6,888,143 B2 | 5/2005 | Vogt et al. | |
| 6,893,388 B2 | 5/2005 | Reising et al. | |
| 6,893,426 B1 | 5/2005 | Popp et al. | |
| 6,915,829 B2 | 7/2005 | Popp et al. | |
| 6,915,929 B2 | 7/2005 | Rauch et al. | |
| 6,919,965 B2 | 7/2005 | Koele et al. | |
| 6,923,798 B2 | 8/2005 | Hedén et al. | |
| 6,976,521 B2 | 12/2005 | Mlinar et al. | |
| 6,976,978 B2 | 12/2005 | Ruman et al. | |
| 6,994,697 B2 | 2/2006 | Shimada et al. | |
| 7,000,260 B2 | 2/2006 | Rajala et al. | |
| 7,039,997 B2 | 5/2006 | Vogt et al. | |
| 7,069,970 B2 | 7/2006 | Tomsovic et al. | |
| 7,077,834 B2 | 7/2006 | Bishop et al. | |
| 7,123,765 B2 | 10/2006 | Carbone, II et al. | |
| 7,132,031 B2 | 11/2006 | Ohiro et al. | |
| 7,150,730 B2 | 12/2006 | Hasler et al. | |
| 7,154,018 B2 | 12/2006 | Koenig et al. | |
| 7,156,833 B2 | 1/2007 | Couture-Dorschner et al. | |
| 7,156,939 B2 | 1/2007 | Vogt et al. | |
| 7,175,584 B2 | 2/2007 | Maxton et al. | |
| 7,195,586 B2 | 3/2007 | Yamamoto et al. | |
| 7,198,622 B2 | 4/2007 | Dahlgren | |
| 7,201,744 B2 | 4/2007 | Van Gompel et al. | |
| 7,207,979 B2 | 4/2007 | Price et al. | |
| 7,214,285 B2 | 5/2007 | Guenther et al. | |
| 7,229,515 B2 | 6/2007 | Couillard et al. | |
| 7,270,631 B2 | 9/2007 | Franklin et al. | |
| 7,297,139 B2 | 11/2007 | Price et al. | |
| 7,318,798 B2 | 1/2008 | Yamamoto et al. | |
| 7,322,925 B2 | 1/2008 | Couillard et al. | |
| 7,322,967 B2 | 1/2008 | Kondo | |
| 7,322,968 B2 | 1/2008 | Shimoe | |
| 7,335,150 B2 | 2/2008 | Coenen et al. | |
| 7,387,148 B2 | 6/2008 | Vogt et al. | |
| 7,390,373 B2 | 6/2008 | Karlsson et al. | |
| 7,407,468 B2 | 8/2008 | Reising et al. | |

(56) References Cited

U.S. PATENT DOCUMENTS

| | | |
|---|---|---|
| 7,425,242 B2 | 9/2008 | Olsson et al. |
| 7,431,791 B2 | 10/2008 | Heller et al. |
| 7,435,245 B2 | 10/2008 | Wendelstorf et al. |
| 7,449,017 B2 | 11/2008 | Yoshida |
| 7,452,320 B2 | 11/2008 | Csida et al. |
| 7,455,665 B2 | 11/2008 | Wendelstorf et al. |
| 7,459,050 B2 | 12/2008 | Karlsson et al. |
| 7,524,313 B2 | 4/2009 | Kline et al. |
| 7,534,237 B2 | 5/2009 | Olson et al. |
| 7,578,812 B2 | 8/2009 | Datta et al. |
| 7,582,076 B2 | 9/2009 | Yoshioka et al. |
| 7,621,901 B2 | 11/2009 | Karami |
| 7,637,898 B2 | 12/2009 | Kuen et al. |
| 7,682,349 B2 | 3/2010 | Popp et al. |
| 7,695,464 B2 | 4/2010 | Fletcher et al. |
| 7,737,324 B2 | 6/2010 | LaVon et al. |
| 7,766,887 B2 | 8/2010 | Burns, Jr. et al. |
| 7,833,207 B2 | 11/2010 | Kenmochi et al. |
| 7,842,849 B2 | 11/2010 | Datta |
| 7,857,801 B2 | 12/2010 | Hamall et al. |
| 7,892,219 B2 | 2/2011 | Ito et al. |
| 7,901,392 B2 | 3/2011 | Kline et al. |
| 7,955,244 B2 | 6/2011 | Burns, Jr. et al. |
| 8,043,273 B2 | 10/2011 | Van Gompel et al. |
| 8,043,274 B2 | 10/2011 | Mlinar et al. |
| 8,053,625 B2 | 11/2011 | Nhan et al. |
| 8,066,686 B2 | 11/2011 | Coomans |
| 2003/0066609 A1 | 4/2003 | Calvert |
| 2003/0168614 A1 | 9/2003 | Vogt et al. |
| 2003/0216706 A1 | 11/2003 | Olsson et al. |
| 2005/0177127 A1 | 8/2005 | Ashton et al. |
| 2005/0256489 A1 | 11/2005 | Sawyer et al. |
| 2005/0277905 A1 | 12/2005 | Pedersen et al. |
| 2007/0049890 A1 | 3/2007 | Popp et al. |
| 2007/0049897 A1 | 3/2007 | Lavon et al. |
| 2007/0113984 A1 | 5/2007 | Pasqualoni |
| 2007/0213678 A1 | 9/2007 | Thorson et al. |
| 2007/0287980 A1 | 12/2007 | Kline et al. |
| 2008/0195074 A1 | 8/2008 | Popp et al. |
| 2008/0249493 A1 | 10/2008 | Kobayashi et al. |
| 2009/0043275 A1 | 2/2009 | Perneborn |
| 2009/0198206 A1 | 8/2009 | Kline et al. |
| 2009/0254059 A1 | 10/2009 | Nilsson et al. |
| 2009/0277564 A1 | 11/2009 | Widlund et al. |
| 2010/0057029 A1 | 3/2010 | Popp et al. |
| 2010/0114048 A1 | 5/2010 | Bishop et al. |
| 2010/0121293 A1 | 5/2010 | Fletcher et al. |
| 2010/0191211 A1 | 7/2010 | Molander |
| 2010/0215908 A1 | 8/2010 | Kline et al. |
| 2010/0215913 A1 | 8/2010 | Kline et al. |
| 2010/0217217 A1 | 8/2010 | Kline et al. |
| 2010/0217219 A1 | 8/2010 | Kline et al. |
| 2010/0217220 A1 | 8/2010 | Kline et al. |
| 2010/0217221 A1 | 8/2010 | Kline et al. |
| 2010/0217222 A1 | 8/2010 | Kline et al. |
| 2010/0262110 A1 | 10/2010 | Lakso |
| 2010/0262112 A1 | 10/2010 | Back et al. |
| 2010/0298803 A1 | 11/2010 | Popp et al. |
| 2010/0305532 A1 | 12/2010 | Ashton et al. |
| 2011/0072561 A1 | 3/2011 | Kinoshita et al. |
| 2011/0082436 A1 | 4/2011 | Meetz et al. |
| 2011/0098668 A1 | 4/2011 | Thorson et al. |
| 2011/0106042 A1 | 5/2011 | Sablone et al. |
| 2011/0114245 A1 | 5/2011 | Nhan et al. |
| 2011/0125125 A1 | 5/2011 | Schneider et al. |

FOREIGN PATENT DOCUMENTS

| | | |
|---|---|---|
| EP | 1289465 B1 | 2/2008 |
| EP | 1289466 B1 | 2/2008 |
| EP | 1284700 B1 | 4/2008 |
| GB | 2244422 | 12/1991 |
| IT | B-195 581 | 1/1983 |
| IT | PE92A000001 | 1/1992 |
| IT | PE2004A000001 | 2/2004 |
| WO | 9317648 | 9/1993 |
| WO | 9529657 | 11/1995 |
| WO | 9621408 | 7/1996 |
| WO | 9818421 | 5/1998 |
| WO | 01/91666 A2 | 12/2001 |
| WO | 2009/083788 A1 | 7/2009 |
| WO | 2010/008032 A1 | 1/2010 |

OTHER PUBLICATIONS

PCT International Search Report and Written Opinion mailed May 2, 2012 for PCT/IB2012/000046.

U.S. Statutory Invention Registration No. H1674 to Ames et al., published Aug. 5, 1997.

Disclosure under 37 CFR 1.56 for U.S. Appl. No. 13/422,248, filed May 24, 2012.

PCT International Search Report and Written Opinion mailed Feb. 25, 2011 for PCT/IB2010/054797.

* cited by examiner

PROCESS AND EQUIPMENT FOR FOLDING A PANT TYPE DIAPER

CROSS REFERENCE TO RELATED APPLICATIONS

This application claims priority to U.S. Provisional Patent Application No. 61/453,677 filed on Mar. 17, 2011, the disclosure of which is incorporated in full herein by reference.

BACKGROUND

The present disclosure relates to a process and apparatus for folding and fastening absorbent products of the pre-closed pant type (commonly referred to as "training pants") which can be used by babies or adults.

Over the last few years, there has emerged interest in diapers of the type commonly referred to as "training pants". When such a product is taken out of the pack, it already has a conformation that substantially resembles that of a pair of pants. It is put on by sliding it over the legs of the user according to criteria basically similar to the ones adopted for putting on pants.

A training pant typically includes a central portion or region that contains an absorbent core which is designed to absorb the bodily fluids evacuated by the wearer. Side panels extend laterally from the central portion so as to complete the pant-like configuration of the product. The side panels are provided with homologous distal edges designed to be connected (pre-fastened) to one another to form lateral closure regions. In the most recent products the pre-fastened closure regions are intended to be refastenable, thus permitting the product—which is sold in a pre-fastened, closed pant-like condition—to be selectively opened at either side in order to check e.g. whether the product is soiled.

Despite recent developments in equipment and methods for folding and fastening training pants, the various arrangements considered in the prior art have an intrinsic disadvantage in that a separate step of fastening of the side panels subsequent to the step of folding the training pant is typically necessary. This additional step adds to the complexity of plants used for production since the associated manufacturing processes and apparatus are inevitably complex, expensive, and exposed to criticalities in terms of reliability.

It would therefore be desirable to provide a solution that enables the fastening of a training pant directly during the step of folding. Such a solution would enable simplification of the plant for production of the folded training pants since a separate station for fastening of the side panels would not be necessary. The claims are an integral part of the disclosure of the invention as provided herein.

SUMMARY OF THE INVENTION

In one aspect, a method of engaging side panels of an absorbent article is provided. The method includes providing a training pant comprising a leading portion, a trailing portion, and a central portion extending in a longitudinal direction between the leading portion and the trailing portion. The training pant further includes a first pair of side panels attached to the central portion proximal one of the leading portion and the trailing portion of the training pant and a second pair of side panels attached to the central portion proximal another of the leading portion and the trailing portion of the training pant. The first pair of side panels each comprises a first fastening region and the second pair of side panels each comprises a second fastening region. The method further includes folding the central portion of the training pant about a transverse axis orthogonal to the longitudinal direction to form a folded training pant. At least a portion of the first fastening regions and at least a portion of the second fastening regions are engaged while the central portion of the folded training pant is received by at least one recessed seat, wherein the at least one recessed seat is located on at least one of a first belt and a second belt of a conveyance system.

In another aspect, an apparatus for preparing a folded training pant is provided. The apparatus includes a conveyance system. The conveyance system comprises a first conveying device comprising a first belt and a second conveying device comprising second belt, wherein the first conveying device and the second conveying device are each configured such that the first belt and the second belt form at least one parallel rectilinear branch. The conveyance system also includes a folding nip, situated between the respective rectilinear branches of the first belt and the second belt and adapted to fold a training pant about a transverse axis orthogonal to a longitudinal direction to form a folded training pant. At least one of the first belt and the second belt further comprises at least one recessed seat configured to receive a central portion of the folded training pant.

In another aspect, an apparatus for preparing a folded training pant is provided. The apparatus includes a training pant assembly system configured to prepare a training pant comprising a leading portion, a trailing portion, and a central portion extending in a longitudinal direction between the leading portion and the trailing portion. The training pant comprises a first pair of side panels attached to the central portion proximal one of the leading portion and the trailing portion of the training pant and a second pair of side panels attached to the central portion proximal another of the leading portion and the trailing portion of the training pant. The first pair of side panels each comprises a first fastening region and the second pair of side panels each comprises a second fastening region. The apparatus also includes a conveyance system comprising a first conveying device comprising a first belt, a second conveying device comprising a second belt, and at least one parallel rectilinear branch between the first belt and the second belt. The conveyance system further includes a folding nip, situated between the respective rectilinear branches and adapted to fold the training pant about a transverse axis orthogonal to the longitudinal direction to form a folded training pant. At least one of the first belt and the second belt also includes at least one recessed seat configured to receive the central portion of the folded training pant.

BRIEF DESCRIPTION OF THE SEVERAL DRAWING VIEWS

The invention will now be described, by way of example only, with reference to the annexed representations, wherein.

DETAILED DESCRIPTION

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms "first" and "second" as used herein in reference to side panels, belts, fastening regions, rectilinear branches, recessed seats, perforations and the like is not intended to refer to any specific order that the components are formed or added to a pant chassis during the manufacturing process or otherwise limit the claims to any specific embodiment illustrated or described herein. Instead, the terms are merely intended to clarify that a referenced component is different than a similar mentioned component.

Process for Folding a Pant Type Diaper

Figure 1:
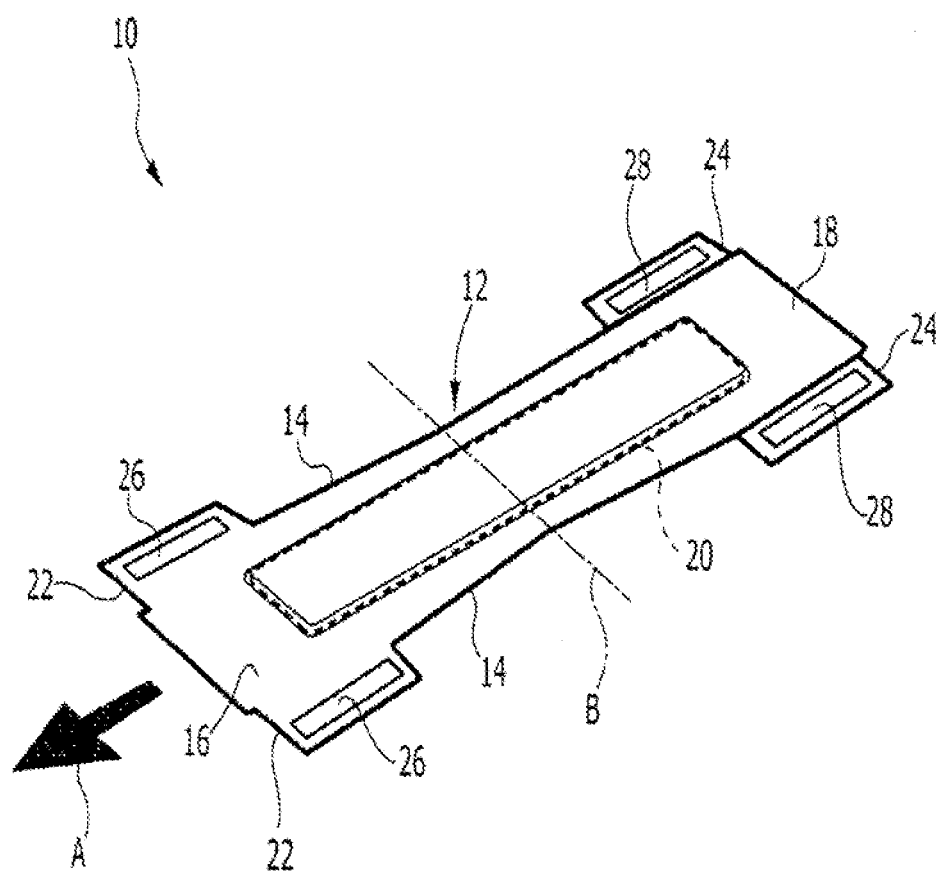
FIG. 1 is a plan view of a training pant in a flattened-out configuration in accordance with one or more embodiments of the present disclosure.

With reference to FIG. 1, a training pant 10 is provided that may be worn by a user like a pair of pants. The training pant 10 comprises a central body 12 having two opposite side edges 14, a leading portion 16, and a trailing portion 18. According to modalities conventional in the sector, the central body 12 comprises an absorbent core 20 that is sandwiched between a topsheet 13 (not shown) that is permeable to the body liquids evacuated and is designed to face the body of the user (body-side), and a backsheet 15 (not shown) that is impermeable to the liquids and is designed to face outwards, i.e., away from the body of the user (clothes-side).

The training pant 10 comprises a first pair of side panels 22 attached proximal to the leading portion 14 and a second pair of side panels 24 attached proximal to the trailing portion 18. Both the first pair of side panels 22 and the second pair of side panels 24 are fixed to respective side edges 14 of the central portion 12. The first pair of side panels and second pair of side panels 22, 24 may be fixed permanently to the respective leading and trailing portions 16, 18 of the central body 12, or may be extensions of the topsheet 13 or of the backsheet 15 or of both. Furthermore, one or more of the side panels may further comprise elastic properties.

It is emphasized that the terms "leading" and "trailing" are used herein merely to distinguish the two ends of the training pant 10 from one another and hence do not have specific significance as regards the modalities with which the product is finally worn. For instance, the leading portion 16 may comprise a front waist region or a back waist region. Similarly, the trailing portion 18 may comprise a back waist region or a front waist region. In all embodiments, however, the training pant 10 includes both a front waist region and a back waist region.

The pairs of first and second side panels 22, 24 are provided with respective first fastening regions 26 and second fastening regions 28 that may form a fastening system. In some embodiments, the fastening system may comprise a refastenable fastening system. In other embodiments, the fastening system may comprise a permanently bonded fastening system. For a refastenable fastening system, at least a portion of the first fastening region 26 co-operates with at least a portion of a corresponding second fastening region 28 to form a refastenable lateral fastening. In some embodiments, the first fastening region 26 comprises a first fastening element and the second fastening region 28 comprises a second fastening element. The fastening regions may also comprise a single fastening element or multiple fastening elements. The fastening elements may comprise any recloseable fastening element suitable for refastenably engaging the pairs of first and second fastening regions 26, 28, such as for example adhesive fastenings, mechanical fastenings, or the like.

In one embodiment, the first and second fastening regions 26, 28 are a refastenable fastening system and comprise complementary fastening elements of the hook-and-loop type (e.g., Velcro®), which may be refastenably engaged to one another when the training pant 10 is folded about a transverse axis B of the training pant 10. In some embodiments, the fastening elements may be fixed on respective opposite internal/external surfaces of the respective pairs of first and second side panels 22, 24. In some embodiments, either the pair of first side panels 22 or the pair of second side panels 24 may comprise a pair of fastening elements that are located on the clothes-side of the respective pair of first side panels 22 or the pair of second side panels 24 to form a pair of clothes-side fastening elements. In such an embodiment, the clothes-side fastening elements may be folded inwardly over the central portion 12 of the training pant 10. In this way, the respective fastening elements of the pair of first side panels 22 may be aligned with the pair of second side panels 24 when the central portion 12 of the training pant 10 is folded about a transverse axis B of the training pant 10.

In still other embodiments, the loop fastening elements may be formed by surface portions of the first fastening region 26 or the second fastening region 28. In yet other embodiments, the loop fastening material may be formed by surface portions of the pair of first side panels 22 or the pair of second side panels 24.

The composition of the materials of the training pant 10 is not described in detail in so far as it departs from the scope of the present disclosure. The pant 10 may be produced with any shape, components, or materials known to those of ordinary skill in the art.

The training pants 10 may be formed starting from a continuous composite web that advances in a longitudinal direction A. The composite web may be formed by a continuous succession of semifinished training pants 10 aligned to one another in the direction A. In the continuous composite web, the training pants 10 are oriented in a direction parallel to the direction of movement of the web. The continuous composite web may be cut in a transverse direction to form discrete training pants 10.

For example, a process for manufacturing a training pant 10 is described in detail in PCT Application No. PCT/IB2010/054797, which is incorporated in its entirety herein by reference.

The training pants 10 initially are in a stretched-out configuration and may then be folded about a line of transverse folding B. As used herein, the term line of transverse folding is equivalent to a transverse axis orthogonal to the longitudinal direction of the training pant 10 ("transverse axis"). Subsequent to the folding of the training pant 10 about the transverse axis, the leading portion 16 and the trailing portion 18 may be positioned on top of one another. Once the training pant 10 is converted to the folded training pant 11, the pair of first fastening regions 26 and the pair of second fastening regions 28 are in a condition where they face one another and the pair of first fastening regions 26 and the pair of second fastening regions 28 may be joined together. In some embodiments, once the training pant 10 is converted to the folded training pant 11, the pair of first fastening elements may be connected to the pair of second fastening elements.

It will be appreciated that after the step of folding the training pant 10 about the transverse axis B to form the folded training pant 11, and following the formation of a connection between the homologous pairs of fastening regions 26, 28 the folded training pant 11 assumes the conformation of a garment that may be worn like a pair of pants. In other embodiments, following the formation of a connection between the homologous pairs of fastening elements, the folded training pant 11 assumes the conformation of a garment that may be worn like a pair of pants.

Apparatus for Folding a Pant Type Diaper

Figure 2:
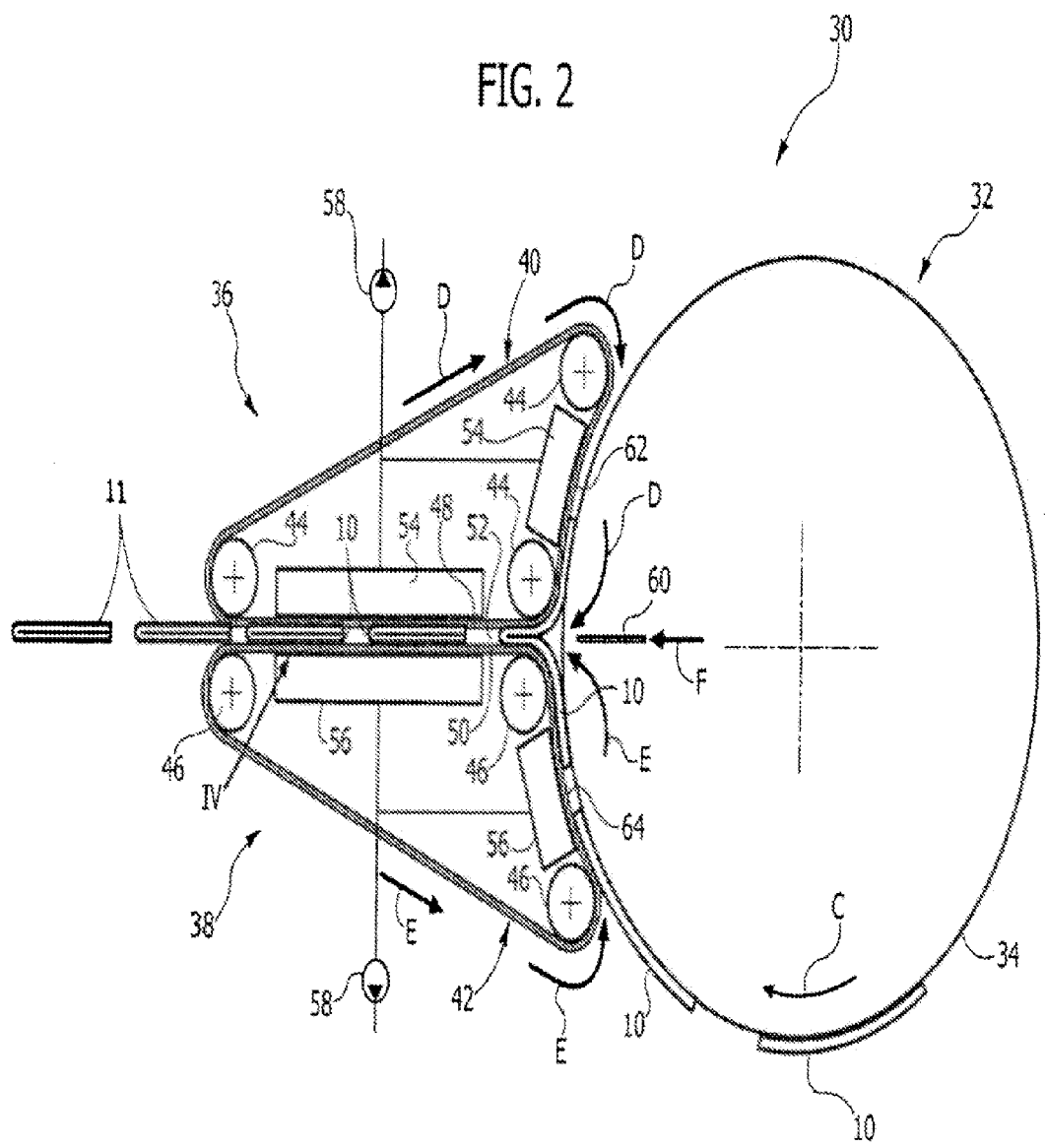
FIG. 2 is a schematic cross-section representation of a method for folding a training pant in accordance with one or more embodiments of the present disclosure.

FIG. 2 is a schematic cross-section representation of a method for folding a training pant. FIG. 2 depicts a folding apparatus 30 for transversely folding the discrete training pants 10 from an initially stretched-out condition to form folded training pants 11. The folding apparatus 30 includes a transfer means, which, in the example illustrated, is formed by a drum roller 32 having an outer surface 34 on which the discrete training pants 10 in a stretched-out condition may be secured to the drum roller 32 during transport to the folding nip 52 using vacuum suction. The drum roller 32 may rotate about a fixed axis in the direction indicated by the arrow C.

The equipment 30 comprises a first conveying device 36 and a second conveying device 38. The first conveying device 36 and the second conveying device 38 have a respective first belt 40 and second belt 42 that are each moved over respective first rollers 44 and second rollers 46. As used herein, the term rollers refers to the pulleys situated in the corners of each conveying device. The first belt 40 and the second belt 42 are moved in the directions indicated by the arrows D and E, respectively. The first belt 40 and the second belt 42 each have at least one respective first rectilinear branch 48 and second rectilinear branch 50 that are situated parallel to one another, thereby forming a folding nip 52.

The first belt 40 and the second belt 42 are configured to pick up by suction respective sections of the training pants 10. To accomplish this result, the first belt 40 and the second belt 42 may be perforated and may be respectively connected to a first suction box 54 and a second suction box 56. The first and second suction boxes 54, 56 may be further connected to a source of negative pressure 58. In some embodiments, the source of negative pressure 58 may be a dynamic vacuum. In other embodiments, the source of negative pressure 58 may be a static vacuum. The first belt 40 and the second belt 42 may each have a respective first branch 62 and second branch 64, each of which face the drum roller 32 and have the purpose of picking up respective sections of the products 10.

The folding apparatus 30 may also be equipped with an insertion blade 60 positioned at the mouth of the folding nip 52 and mobile in the direction indicated by the arrow F to facilitate insertion of the training pants 10 into the folding nip 52. In some embodiments, the insertion blade 60 may facilitate the insertion of the central portion 12 of the training pant 10 into the folding nip 52. In other embodiments, the insertion blade 60 may facilitate the insertion of a midpoint of the central portion 12 of the training pant 10 into the folding nip 52. As used herein, the midpoint of the central portion 12 of the training pant 10 is defined as being located substantially close to the transverse axis B of the training pant 10.

Operation of the folding apparatus 30 is now described. The discrete training pants 10, secured in a spread-out position on the outer surface 34 of the drum roller 32, are brought into contact with both the first branch 62 and the second branch 64 of the respective first belt 40 and second belt 42. In some embodiments, the leading portion 16 of the training pant 10 may be brought into contact with the first branch 62 of the first belt 40 and the trailing portion 18 of the same training pant 10 may be brought into contact with the second branch 64 of the second belt 42. The leading portion 16 and the trailing portion 18 of the training pant 10 may be picked up by vacuum suction by the first and second branches 62, 64 of the respective first and second belts 40, 42, and the central portion 12 of the training pant 10 may be inserted into the folding nip 52. In some embodiments, the insertion blade 60 may push the central portion 12 of the training pant 10 in the direction F to facilitate insertion of the product into the folding nip 52. Each training pant 10 may then move through the folding nip 52 and be folded along the transverse axis B to form the folded training pant 11. The leading portion 16 and the trailing portion 18 of each training pant 10 are positioned on top of one another during the passage of the training pant 10 through the folding nip 52. During folding, the pair of first fastening regions 26 and the pair of second fastening regions 28 may be pressed into contact with one another. In still other embodiments, during folding the pair first fastening elements and the pair of second fastening elements may be pressed into contact with one another.

Figure 3:
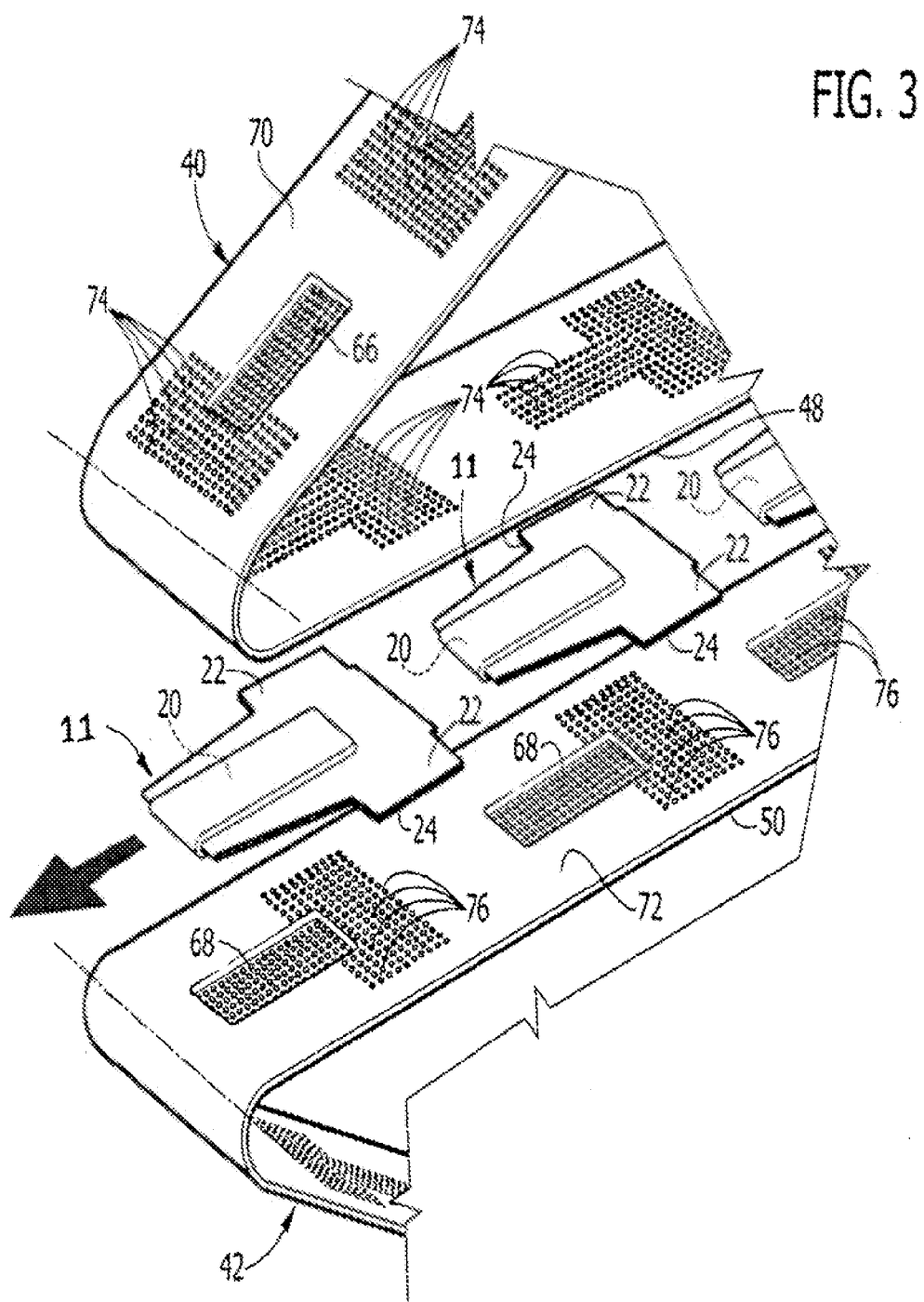
FIG. 3 is a partially exploded perspective view of a folded training pant positioned between a first belt and a second belt according to one or more embodiments of the present disclosure.
Figure 4:
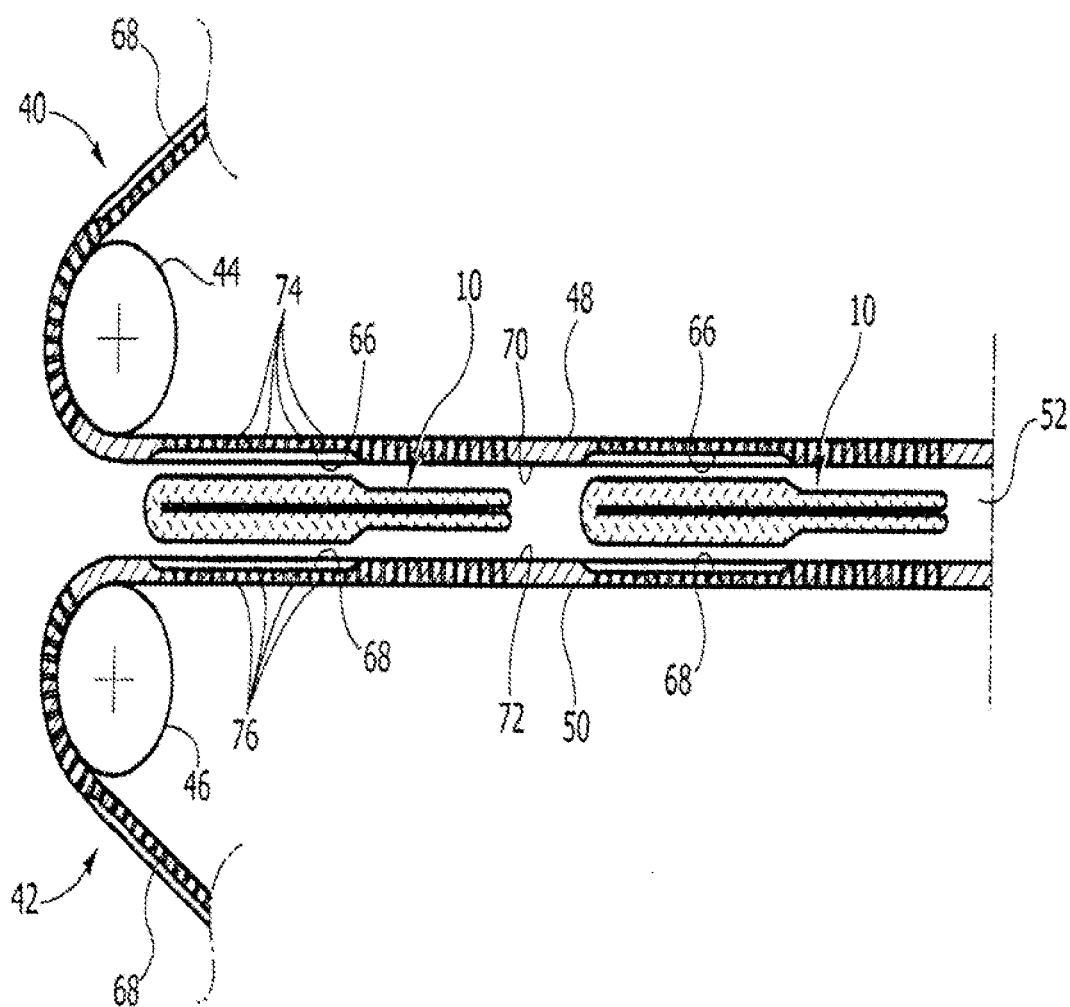
FIG. 4 is a partial schematic cross-section representation of a method for manufacturing a folded training pant in accordance with one or more embodiments of the present disclosure.

With reference to FIGS. 3 and 4, at least one of the first belt 40 and the second belt 42 may respectively include first perforated regions 74 and second perforated regions 76 which may be used to secure the folded training pants 10 to the respective first and second belts 40, 42. The central portion 12 of the training pants 10 may be received into a first recessed seat 66 or a second recessed seat 68 or both. As used herein, the term recessed seat means that the seats are recessed with respect to the respective first outer surface 70 and second outer surface 72 of the respective first belt 40 and second belt 42. In the example illustrated in FIGS. 3 and 4, both the first belt 40 and the second belt 42 are provided with respective recessed seats 66, 68. In other embodiments, only one of the first belt 40 and the second belt 40 may include a recessed seat.

The areas for securing the folded training pants 11 may be provided by the first perforated regions 74 and the second perforated regions 76, which are each configured to secure the folded training pants 10 by vacuum suction. The arrangement of the perforations in the first perforated regions 74 and the second perforated regions 76 may be such as to reproduce the shapes of the respective leading portion 16 and trailing portion 18 of the folded training pant 11. The first recessed seats 66 and the second recessed seats 68 each receive respective portions of the central portion 12 of the folded training pant 11 in which the absorbent core 20 is present. In one embodiment, the pair of first side panels 22 and the pair of second side panels 24 of each folded training pant 11 are arranged on the outside of the respective first recessed seats 66 and second recessed seats 68. In some embodiments, the pair of first side panels 22 and the pair of second side panels 24 of each folded training pant 11 may be situated on the first outer surface 70 and the second outer surface 72, respectively. In some embodiments, the pair of first side panels 22 and the pair of second side panels 24 of each folded training pant 11 may be secured to the first outer surfaces 70 and the second outer surfaces 72, respectively, using vacuum suction. In some embodiments, the first outer surfaces 70 and the second outer surfaces 72 may further include perforations to facilitate vacuum suction.

In a further embodiment, wherein only one of the first belt 40 or the second belt 42 includes respective first recessed seats 66 or second recessed seats 68, at least one of the pair of first side panels 22 or the pair of second side panels 24 of the folded training pant 11 is positioned on the respective first outer surface 70 or the second outer surface 72. In such an embodiment, where the central portion 12 of the folded training pant 11 is situated in a recessed seat located on only one belt, the other belt is configured to situate both the central portion 12 of the folding training pant 11 and the other pair of side panels on the smooth surface of the other belt that is without the recessed seats. Both of the other pair of side panels and the central portion 12 of the folded training pant 11 are secured in position by means of the grip generated by the perforated areas to which vacuum suction may be applied.

FIG. 4 is a partial schematic cross-section representation of a method for manufacturing a folded training pant and illustrates the folded training pants 11 moving in a machine direction F after completely passing through the folding nip 52. For simplicity, FIG. 4 shows the first rectilinear branch 48 and the second rectilinear branch 50 of the respective first belt 40 and the second belt 42, set at an exaggerated distance apart from one another. In practice, the facing first outer surface 70 and the second outer surface 72 of the respective first rectilinear branch 48 and the second rectilinear branch 50 are positioned close to one another and compress between them the pair of first side panels 22 with the pair of second side panels 24, wherein the pairs of side panels 22, 24 are situated on top of one another so as to maintain mutual compression of the pair of first side panels 22 with the pair of second side panels 24. In some embodiments, the pairs of side panels 22, 24 are situated on top of one another so as to maintain mutual compression and refastenable securement of the pair of first fastening elements with the pair of complementary second fastening elements.

In FIG. 4, the central portions 12 are situated within the first recessed seats 66 and the second recessed seats 68. An advantage of positioning the thicker parts (i.e., central portions 12) of the folded training pants 11 within the recessed seats 66, 68 enables application of the desired contact and compression pressures on the side panels 22, 24 and on the fastening regions 26, 28 without unnecessarily squeezing the central portions 12 of the folded training pants 11 in which the absorbent core 20 is set.

This apparatus and the method have a further advantage of fastening of the training pants 10 directly during the step of folding. A separate step of fastening of the side panels subsequent to the step of folding is thus avoided. This solution therefore enables simplification of the plant for production of the folded training pants 11 since a separate station for fastening of the side panels is not necessary.

In some embodiments, the movement of the first belt 40 and the movement of the second belt 42 are in phase with one another in such a way that the first recessed seats 66 and the second recessed seats 68 face one another as the respective belts move through the folding nip 52. Moreover, the movement of the first belt 40 and the movement of the second belt 42 are in phase with the rotation of the drum roller 32 in such a way that the central portions 12 of the training pants 10 are inserted into the folding nip 52 in alignment with first recessed seats 66 and the second recessed seats 68.

In still other embodiments, at least one of the first suction box 54 and the second suction box 56 are connected to the vacuum source 58 by a connection system adapted to activate and deactivate the vacuum suction in phase with the movement of the training pant 10.

In another embodiment, the folding apparatus 30 may be configured to handle training pants 10 lacking refastenable elements and may be adapted to form permanent and/or non-refastenable engagement seams between the pair of first fastening regions 26 and the pair of second fastening regions 28. In some embodiments, opposing sealing rollers (not shown) may be incorporated into at least one of the first conveying device 36 and the second conveying device 38. In some embodiments, the opposing sealing rollers may form the folding nip 52. In other embodiments, the opposing sealing rollers may be situated at a location downstream of the folding nip 52. In still other embodiments, the opposing sealing rollers may be aligned at locations transverse to the machine direction and corresponding to the desired location of the sealed engagement seams. In yet other embodiments, the opposing sealing rollers may provide sufficient pressure and/or heat to create a non-refastenable engagement seam between the pair of first fastening regions 26 and the pair of second fastening regions 28. In other embodiments, alternate means may be employed for producing non-refastenable engagement seams, including but not limited to ultrasonic bonding, hydroentangling, adhesive bonding, and the like.

In certain embodiments, the sealing rollers may be configured to be removable from the folding apparatus 30 so that the folding apparatus 30 may be capable of selectively and alternately producing refastenable and non-refastenable training pants with minimal modification to the production line and minimal machine down time. Accordingly, the folding apparatus 30 may be operable with or without the sealing rollers being present.

Of course, without prejudice to the underlining principles of the invention, the details and embodiments may vary, even significantly, with respect to what has been described and illustrated herein merely by way of example, without departing from the scope of the invention as defined by the annexed claims.

We claim:

1. A method of engaging side panels of an absorbent article comprising:
   providing a training pant comprising a leading portion, a trailing portion, and a central portion extending in a longitudinal direction between the leading portion and the trailing portion, the training pant comprising a first pair of side panels attached to the central portion proximal one of the leading portion and the trailing portion of the training pant and a second pair of side panels attached to the central portion proximal another of the leading portion and the trailing portion of the training pant, wherein the first pair of side panels each comprise a first fastening region and the second pair of side panels each comprise a second fastening region;
   folding the central portion of the training pant about a transverse axis orthogonal to the longitudinal direction to form a folded training pant; and
   engaging at least a portion of the first fastening regions and at least a portion of the second fastening regions while the central portion of the folded training pant is received by at least one recessed seat, wherein the at least one recessed seat is located on at least one of a first belt and a second belt of a conveyance system.

2. The method of claim 1, wherein the conveyance system comprises:
   a first conveying device comprising a first belt; and
   a second conveying device comprising a second belt;
   wherein the first conveying device and the second conveying device are each configured such that the first belt and the second belt form at least one parallel rectilinear branch.

3. The method of claim 2, wherein the first belt and the second belt move in phase.

4. The method of claim 2, wherein the at least one parallel rectilinear branch forms a folding nip between the first belt and the second belt.

5. The method of claim 4, wherein the step of folding further comprises transferring the training pant from a drum roller to the folding nip.

6. The method of claim 5, wherein the step of transferring further comprises inserting the central portion of the training pant into the folding nip.

7. The method of claim 6, wherein the step of inserting the central portion of the training pant into the folding nip further comprises using an insertion blade to push the central portion of the training pant into the folding nip.

8. The method of claim 5, wherein the step of transferring further comprises inserting a midpoint of the central portion of the training pant into the folding nip.

9. The method of claim 8, wherein the step of inserting the midpoint of the central portion of the training pant into the folding nip further comprises using an insertion blade to push the midpoint of the central portion of the training pant into the folding nip.

10. The method of claim 4, wherein the step of folding further comprises moving the central portion of the training pant through the folding nip to form the folded training pant.

11. The method of claim 4, wherein the step of folding further comprises moving a midpoint of the central portion of the training pant through the folding nip to form the folded training pant.

12. The method of claim 4, wherein the step of folding further comprises inserting the central portion of the training pant into the folding nip using an insertion blade.

13. The method of claim 4, wherein the step of folding further comprises inserting the midpoint of a central portion of the training pant into the folding nip using an insertion blade.

14. The method of claim 1, wherein the step of folding further comprises situating at least a portion of the central portion of the training pant on the at least one recessed seat.

15. The method of claim 1, further comprising transporting the folded training pant in a machine direction while the central portion of the folded training pant is situated within the at least one recessed seat on the at least one of the first belt and the second belt.

16. The method of claim 15, wherein the first belt comprises the at least one recessed seat and the second belt comprises the at least one other recessed seat and the central portion of the folded training pant is received by both the at least one recessed seat and the other at least one recessed seat.

17. The method of claim 15, wherein the step of transporting the folded training pant further comprises gripping the folded training pant to the at least one of the first belt and the second belt using a vacuum connected to one or more perforations in the respective at least one of the first belt and the second belt.

18. The method of claim 17, further comprising gripping the folded training pant to the first belt using a vacuum connected to one or more perforations in the first belt and gripping the folded training pant to the second belt using a vacuum connected to one or more perforations in the second belt.

19. The method of claim 15, wherein the at least one recessed seat comprises one or more perforations adapted to grip the central portion of the training pant using vacuum suction.

20. The method of claim 15, wherein the at least one of the first belt and the second belt is a motor-powered belt.

21. The method of claim 15, wherein the first belt is a motor-powered belt and the second belt is a motor-powered belt.

22. The method of claim 1, wherein the step of engaging further comprises refastenably engaging the at least a portion of the first fastening regions and the at least a portion of the second fastening regions.

23. The method of claim 22, wherein the first fastening regions comprise first fastening components and the second fastening regions comprise second fastening components.

24. The method of claim 23, wherein the first fastening components are hook-type fastening components and the second fastening components are loop-type fastening components.

25. The method of claim 22, wherein the step of engaging further comprises pressing the at least a portion of the first fastening regions and the at least a portion of the second fastening regions together using the folding nip.

26. The method of claim 1, wherein the step of engaging further comprises permanently engaging the at least a portion of the first fastening regions and the at least a portion of the second fastening regions.

27. The method of claim 26, wherein the step of permanently engaging comprises thermal bonding, ultrasonic bonding, hydroentangling, adhesive bonding, and combinations thereof.

28. The method of claim 1, wherein the step of folding further comprises positioning at least one side panel of the first pair of side panels and at least one side panel of the second pair of side panels on an outside region of the at least one of a first belt and a second belt, wherein the outside region of the at least one of a first belt and a second belt does not comprise the at least one recessed seat.

29. The method of claim 28, wherein the outside region comprises one or more perforations adapted to grip the at least one side panel of the first pair of side panels and at least one side panel of the second pair of side panels of the training pant using vacuum suction.

30. An apparatus for preparing a folded training pant comprising:
 a conveyance system comprising:
  a first conveying device comprising a first belt;
  a second conveying device comprising second belt, wherein the first conveying device and the second conveying device are each configured such that the first belt and the second belt form at least one parallel rectilinear branch; and
  a folding nip, situated between the respective rectilinear branches of the first belt and the second belt and adapted to fold a training pant about a transverse axis orthogonal to a longitudinal direction to form a folded training pant;
  wherein at least one of the first belt and the second belt further comprises at least one recessed seat configured to receive a central portion of the folded training pant.

31. The apparatus of claim 30, wherein the first conveying device further comprises two or more first rollers.

32. The apparatus of claim 31, wherein the second conveying device further comprises two or more second rollers.

33. The apparatus of claim 32, further comprising a drum roller adapted to transfer the training pant to the conveyance system.

34. The apparatus of claim 33, wherein the central portion of the training pant is inserted from the drum roller into the folding nip.

35. The apparatus of claim 33, wherein a midpoint of the central portion of the training pant is inserted from the drum roller into the folding nip.

36. The apparatus of claim 33, further comprising an insertion blade adapted to insert the central portion of the training pant from the drum roller into the folding nip.

37. The apparatus of claim 33, further comprising an insertion blade adapted to insert a midpoint of the central portion of the training pant from the drum roller into the folding nip.

38. The apparatus of claim 32, wherein the conveyance system further comprises a motor for moving at least one of the first belt and the second belt.

39. The apparatus of claim 32, wherein the conveyance system comprises a first motor for moving the first belt and a second motor for moving the second belt.

40. The apparatus of claim 30, wherein the folding nip is further adapted to press at least a first portion of the first fastening region of the folded training pant together with at least a first portion of the second fastening region of the folded training pant.

41. The apparatus of claim 30, wherein the first belt and the second belt are configured to move in phase.

42. The apparatus of claim 30, wherein at least one of the first belt and the second belt further comprises one or more perforations connected to a vacuum adapted to grip the folded training pant.

43. The apparatus of claim 42, wherein the one or more perforations are located within the at least one recessed seat of the at least one of the first belt and the second belt.

44. The apparatus of claim 43, wherein the first belt comprises at least one recessed seat and the second belt comprises at least one other recessed seat and the central portion of the folded training pant is received by both the at least one recessed seat and the other at least one recessed seat.

45. The apparatus of claim 30, wherein the first belt comprises at least one first recessed seat and the second belt comprises at least one second recessed seat.

46. The apparatus of claim 30, wherein the at least one of the first belt and the second belt further comprises an outside region adapted to transport at least one side panel of a first pair of side panels and at least one side panel of a second pair of side panels in a machine direction, wherein the outside region does not comprise the recessed seat.

47. The apparatus of claim 46, wherein the outside region of the at least one of the first belt and the second belt comprises one or more perforations connected to a vacuum and adapted to grip the at least one side panel of the first pair of side panels and the at least one side panel of the second pair of side panels.

48. The apparatus of claim 30, wherein the first belt and the second belt are further adapted to transport the folded training pant in a machine direction.

49. The apparatus of claim 48, wherein the central portion of the folded training pant is situated within the at least one recessed seat of the at least one of the first belt and the second belt.

50. The apparatus of claim 49, wherein the central portion of the folded training pant is situated within the at least one first recessed seat of the first belt and within the at least one second recessed seat of the second belt.

51. An apparatus for preparing a folded training pant comprising:
   a training pant assembly system configured to prepare a training pant comprising a leading portion, a trailing portion, and a central portion extending in a longitudinal direction between the leading portion and the trailing portion, the training pant comprising a first pair of side panels attached to the central portion proximal one of the leading portion and the trailing portion of the training pant and a second pair of side panels attached to the central portion proximal another of the leading portion and the trailing portion of the training pant, wherein the first pair of side panels each comprise a first fastening region and the second pair of side panels each comprise a second fastening region;
   a conveyance system comprising:
      a first conveying device comprising a first belt;
      a second conveying device comprising a second belt;
      at least one parallel rectilinear branch between the first belt and the second belt; and
      a folding nip, situated between the respective rectilinear branches and adapted to fold the training pant about a transverse axis orthogonal to the longitudinal direction to form a folded training pant;
      wherein at least one of the first belt and the second belt further comprises at least one recessed seat configured to receive the central portion of the folded training pant.

52. The apparatus of claim 51, wherein the first conveyance system further comprises two or more first rollers.

53. The apparatus of claim 52, wherein the second conveyance system further comprises two or more second rollers.

54. The apparatus of claim 51, wherein the folding nip is further adapted to press at least a first portion of the first fastening region of the folded training pant together with at least a first portion of the second fastening region of the folded training pant.

55. The apparatus of claim 51, wherein the first belt and the second belt are further configured to move in phase.

56. The apparatus of claim 51, wherein the at least one of the first belt and the second belt further comprises one or more perforations connected to a vacuum and adapted to grip at least portions of at least one of the training pant and the folded training pant.

57. The apparatus of claim 54, wherein the one or more perforations are situated within the at least one recessed seat of the at least one of the first belt and the second belt.

58. The apparatus of claim 51, further comprising an insertion blade adapted to insert the central portion of the training pant into the folding nip.

59. The apparatus of claim 51, further comprising an insertion blade adapted to insert a midpoint of the central portion of the training pant into the folding nip.

60. The apparatus of claim 51, wherein at least one of the first conveying device and the second conveying device further comprises a motor for moving at least one of the respective first belt and second belt.

61. The apparatus of claim 51, wherein the first conveying device comprises a first motor for moving the first belt and the second conveying device comprises a second motor for moving the second belt.

62. The apparatus of claim 51, further comprising a drum roller adapted to transport the training pant to the folding nip.

63. The apparatus of claim 51, wherein at least one of the first belt and the second belt further comprises an outside region adapted to transport at least one of the side panels of the first pair of side panels and at least one of the side panels of the second pair of side panels in a machine direction, wherein the outside region does not comprise the at least one recessed seat.

64. The apparatus of claim 63, wherein the outside region of the at least one of the first belt and the second belt comprises one or more perforations connected to a vacuum and adapted to grip the at least one side panel of the first pair of side panels and the at least one side panel of the second pair of side panels.

65. The apparatus of claim 51, wherein the first belt and the second belt are further adapted to transport the folded training pant in a machine direction.

66. The apparatus of claim 65, wherein the central portion of the folded training pant is situated within the at least one recessed seat of the at least one of the first belt and the second belt.

67. The apparatus of claim 65, wherein the central portion of the folded training pant is situated within the at least one first recessed seat of the first belt and within the at least one second recessed seat of the second belt and the central portion of the folded training pant is received by both the at least one first recessed seat and the at least one second recessed seat.

* * * * *